(12) United States Patent
Mulqueen et al.

(10) Patent No.: US 8,808,720 B2
(45) Date of Patent: Aug. 19, 2014

(54) FORMULATION

(75) Inventors: Patrick Joseph Mulqueen, Bracknell (GB); Anne Waller, Bracknell (GB); Julia Lynne Ramsay, Bracknell (GB); Geoffrey William Smith, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 1059 days.

(21) Appl. No.: 12/097,943

(22) PCT Filed: Dec. 22, 2006

(86) PCT No.: PCT/GB2006/004912
§ 371 (c)(1),
(2), (4) Date: Sep. 10, 2008

(87) PCT Pub. No.: WO2007/072052
PCT Pub. Date: Jun. 28, 2007

(65) Prior Publication Data
US 2009/0226496 A1    Sep. 10, 2009

(30) Foreign Application Priority Data
Dec. 23, 2005   (GB) .................... 0526416.3

(51) Int. Cl.
| | | |
|---|---|---|
| *A01N 25/32* | (2006.01) | |
| *A01N 25/00* | (2006.01) | |
| *A01N 25/28* | (2006.01) | |
| *A01N 43/40* | (2006.01) | |
| *A01N 43/50* | (2006.01) | |
| *A01N 43/78* | (2006.01) | |
| *A01N 43/88* | (2006.01) | |

(52) U.S. Cl.
CPC .............. *A01N 25/32* (2013.01); *A01N 25/006* (2013.01); *A01N 25/28* (2013.01); *A01N 43/40* (2013.01); *A01N 43/50* (2013.01); *A01N 43/78* (2013.01); *A01N 43/88* (2013.01)
USPC .......... 424/406; 71/64.13; 504/100; 504/101; 504/103; 504/113; 504/114; 504/116.1; 424/405; 424/408; 424/417; 424/419; 514/341; 514/342; 514/357; 514/365

(58) Field of Classification Search
CPC ..... A01N 25/32; A01N 25/006; A01N 25/28; A01N 43/40; A01N 43/50; A01N 25/4378; A01N 43/88
USPC ................ 424/406, 405, 408, 409, 417, 419; 71/64.13; 504/100, 103, 113, 114, 504/116.1; 514/341, 342, 357, 365
See application file for complete search history.

(56) References Cited

U.S. PATENT DOCUMENTS 6,730,635 B2   5/2004  Wolf et al.
7,070,795 B1 *  7/2006  Botts et al. .................... 424/409

(Continued)

FOREIGN PATENT DOCUMENTS

CA     2385991     12/2001
WO     9220771    11/1992

(Continued)

OTHER PUBLICATIONS

Jabberi, "Morphology and Structure of Microcapsules Prepared by Interfacial Polycondensaton of Methylene bis (phenyl isocyanate) with Hexamethylene Diamine", J. Microencapsulation vol. 18, 2001, pp. 801-809.
Ramarao et al, "Encapsulation of Palladium in Polyurea Microcapsules", Chem. Commun., 2002, pp. 1132-1133.

*Primary Examiner* — Neil Levy
(74) *Attorney, Agent, or Firm* — James Cueva

(57) ABSTRACT

A product comprising microcapsules which themselves comprise (a) a polymeric shell; and (b) a core which comprises (i) a solid agrochemical dispersed in a matrix and (ii) a water-immiscible liquid characterized in that the matrix is distributed non-continuously throughout the water-immiscible liquid.

24 Claims, 2 Drawing Sheets

(56) References Cited

U.S. PATENT DOCUMENTS

Figure 1:
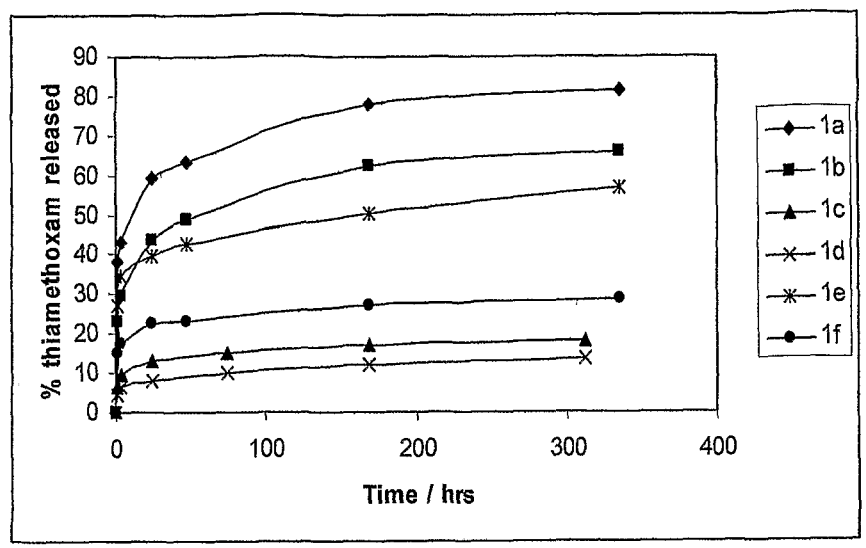

2002/0136773 A1 9/2002 Scher et al.
2003/0119675 A1 6/2003 Wolf et al.
2009/0269382 A1* 10/2009 Mulqueen et al. ............ 424/408

FOREIGN PATENT DOCUMENTS

| WO | 95/13698 | 5/1995 |
| WO | 02060573 | 8/2002 |
| WO | 2005063016 | 7/2005 |

* cited by examiner

FORMULATION

This application is a 371 of International Application No. PCT/GB2006/004912 filed Dec. 22, 2006, which claims priority to GB 0526416.3 filed Dec. 23, 2005, the contents of which are incorporated herein by reference.

This invention relates to novel microcapsules which comprise a solid water-soluble, biologically active compound dispersed in a (non-continuous) matrix which is at least partially solid and which is distributed throughout the microcapsules, and processes for the preparation and for the use of such microcapsules. In particular it relates to a product comprising microcapsules which themselves comprise
(a) a polymeric shell; and
(b) a core which comprises (i) a solid agrochemical dispersed in a matrix and (ii) a water-immiscible liquid characterised in that the matrix is distributed non-continuously throughout the water-immiscible liquid.

Microcapsule technology has been in existence for a number of years. Microcapsules have a variety of uses, especially for containing dyes, inks, chemical reagents, pharmaceuticals, flavouring materials, and more especially agrochemicals, that is fungicides, bactericides, insecticides, herbicides and the like.

Microencapsulated formulations of agrochemicals may be exploited in a wide range of applications both in crop protection and professional products outlets, and may be applied via a variety of methods such as foliar sprays, soil application and as seed treatments. Such formulations allow the release rate of the agrochemical to be controlled over a desired period of time and find applications for weed, fungal or insect control, as termiticides, residual sprays, turf treatments and as seed treatments (amongst others).

In commercial use, agrochemical products are subject to a range of environmental factors which result in a reduction in efficacy of the formulation, including run-off and leaching from soil (which may lead to groundwater contamination), rainfastness and wash-off from seeds; water-soluble active compounds are particularly susceptible to such losses.

The microcapsules of this invention are useful for controlling the release rate of the solid water-soluble biologically active compound, where the biologically active compound is a pesticide [agrochemical], and are particularly useful for controlling the release into any medium where water is present, eg. release of pesticidally active compounds into soil. The microcapsules are even more particularly useful for controlling the release of water-soluble pesticidally active compounds into soil with a high moisture content as a result of heavy rainfall or excessive irrigation. A further advantage is that such products can also reduce the amount of water soluble product that is leached to lower soil levels by heavy rainfall or irrigation.

Such uses may include application of these products in crop protection for the use of insecticides in vegetable crops to extend the performance of a product in soil; use of such a product to provide long term release characteristics in specific market sectors such as control of termites; use of such a product to increase the period of performance on turf, when formulated together with fertilisers as a granule, or applied directly to turf by an appropriate application method and which is then subjected to high levels of irrigation (as commonly employed on golf-courses); use of such products for the protection of seeds where applied prior to sowing and combined with appropriate inerts to provide efficient coating of the seeds; and use of such a product to provide a longer lasting residual deposit where a long lasting deposit may be required.

Several technologies are commonly known as being useful in the production of microcapsules (for example as described in chapter 4 of "Controlled Delivery of Crop Protection Agents", pub. Taylor and Francis, London 1990). One such technology of particular utility for the encapsulation of agrochemicals is interfacial polymerisation in which the walls of the microcapsules are generally formed of polymeric material produced by a polymerisation reaction which preferably takes place at the interface between two phases, usually an aqueous phase and a water-immiscible organic phase. Thus, they may be produced from a water-in-oil emulsion or more usually an oil-in-water emulsion.

Microcapsules which comprise, in the organic phase, suspensions of solid biologically active compounds in organic solvents or liquid biologically active compounds are known (e.g. as described in patent documents WO 95/13698, EP 0730406, U.S. Pat. Nos. 5,993,842 and 6,015,571, the contents of which are fully incorporated herein by reference).

Processes for the microencapsulation of water-soluble biologically active compounds are also known, but in these the biologically active compound is generally dissolved in water or a water-miscible solvent prior to encapsulation.

It has now been found that it is possible to encapsulate solid water-soluble biologically active compounds which are dispersed in a substantially water-immiscible phase, in which the biologically active compound is dispersed in a (non-continuous) matrix which is at least partially solid and which is distributed throughout the microcapsules.

In one particular embodiment, the (non-continuous) matrix is formed via an interfacial polymerisation of an oil-in-water emulsion, in which the solid water-soluble biologically active material is dispersed within the oil. Surprisingly, in this invention carrying out said interfacial polymerisation results in the formation of a polymer (non-continuous) matrix which is distributed throughout the microcapsules, rather than being restricted to the interface, as is commonly taught in the prior art.

There are several problems which must be overcome for the successful encapsulation of a suspension of solid particles within a microcapsule formed by interfacial polymerisation of an oil-in-water emulsion.

Firstly, a stable suspension of the solid in a substantially water-immiscible liquid must be produced. If dispersants or surfactants are used, they must not interfere with any further processes of dispersion used in making microcapsules.

Secondly, the suspension must be dispersed in water to produce stable, well dispersed droplets. For biologically active substances, it is preferable to have very small droplets of liquid dispersed in water so as to present a high surface area of the resulting microcapsules. To produce very small droplets requires high shear forces which would tend to break down the droplets and/or release the solid from suspension. Surfactants are usually required to achieve good dispersion and stable droplets.

Thirdly, the presence of one or more surfactants may make the dispersed droplet system unstable and the phenomenon of phase inversion may occur, i.e. water forms small droplets within the liquid; a water-in-oil emulsion.

Fourthly, the solid suspended in the water-immiscible liquid is liable to migrate to the aqueous phase, particularly when emulsifying surfactants are used.

The last three of these problems is even more challenging to overcome for the encapsulation of water-soluble biologically active compounds, and it has been found that modifications are required to the procedures described in patent documents WO 95/13698, EP 0730406, U.S. Pat. Nos. 5,993,842, 6,015,571, US 2003/0119675 and JP 2000247821 for the encapsulation of suspensions of water-insoluble compounds.

It has now been found that it is possible to produce microcapsules which comprise a solid water-soluble, biologically active compound dispersed in a (non-continuous) matrix which is at least partially solid and which is distributed throughout the microcapsules. Moreover it has been found that the release rate of the biologically active compound can be varied over an extremely wide range; surprisingly very slow release rates into aqueous media are possible despite the water-solubility of the compound. This confers useful benefits to products utilising such technology.

One very suitable technique for the formation of said microcapsules is interfacial polymerisation via an oil-in-water emulsion; surprisingly, this results in the formation of a polymer (non-continuous) matrix which is distributed throughout the microcapsules, rather than being restricted to the interface, as is commonly taught in the prior art.

The microcapsules may be produced using the following methodology:

Step 1—producing the solid water-soluble, biologically active compound with the required particle size, suitably by a milling process. A suitable Volume Median Diameter [VMD] particle size of the solid is 0.01-50 µm; more suitably the lower limit is 0.5 µm and even more suitably the lower limit is 1.0 µm; more suitably the upper limit is 10 µm and even more suitably the upper limit is 5 µm.

Step 2—suspending the solid water-soluble, biologically active compound in a substantially water-immiscible liquid. The liquid is preferably a poor solvent for the solid, i.e. it will not dissolve significant quantities of the solid.

The liquid preferably contains a dispersant capable of keeping the solid in the liquid but which does not allow the solid to be extracted into the water when the suspension is dispersed into water. In addition, when the suspension is added to water, the dispersant must not allow phase inversion to occur.

Alternatively, the procedures of steps 1 and 2 may be varied by performing a milling process to reduce the particle size of the solid water-soluble, biologically active compound, after the compound has been suspended in the substantially water-immiscible liquid (media milling).

Step 3—a physical dispersion of the organic phase in an aqueous phase is prepared. To obtain the appropriate dispersion, the organic phase is added to the aqueous phase, with stirring. A suitable dispersing means is employed to disperse the organic phase in the aqueous phase. Selection of dispersion process and apparatus will depend upon the desired particle size of the emulsion (and ultimate product) to be produced. One suitable means of dispersion is typically a high shear rotor/stator device (such as a laboratory Silverson™ machine) for small (<10 micron VMD products) but other means can be employed such as Cowles™ dissolvers, simple mixing devices for larger particle sizes and even high pressure homogenisation equipment. Choice of such equipment is within the scope of one skill in the art. A suitable means may be any high shear device so as to obtain a desired droplet (and corresponding microcapsule particle) size within the range from about 1 to about 200 µm. A suitable means may be any high shear device so as to obtain a desired droplet (and corresponding microcapsule particle) size within the range from about 1 to about 200 µm; suitably from about 1 to 150 µm; more suitably from about 1 to about 50 µm; and most suitably from about 3 to about 50 µm, VMD. Once the desired droplet size is obtained, the dispersion means is discontinued. Only mild agitation is required for the remainder of the process. The organic phase comprises the solid water-soluble, biologically active compound suspended in the substantially water-immiscible liquid to be encapsulated prepared as described above in steps 1 and 2. The aqueous phase comprises water and at least one emulsifier and/or protective colloid.

Clearly there is a relationship between the particle size of the solid water-soluble, biologically active compound and the particle size of the microcapsules; in order to obtain control over the release rate of the biologically active compound, the VMD ratio of the particle size of this compound to that of the microcapsules will be typically of the value 1:5; suitably in the range 1:3 to 1:100; more suitably 1:5 to 1:20.

In order to obtain the microcapsules, the organic phase and/or the aqueous phase must contain one or more materials which can react to form a polymer. In one preferred embodiment, the organic phase contains at least one diisocyanate and/or polyisocyanate, whilst the aqueous phase contains at least one diamine and/or polyamine. In the situation where at least one diamine and/or polyamine is included in the aqueous phase, this component is added to the aqueous phase after the formation of the oil-in-water emulsion as described above in step 3.

Step 4—at least one diamine and/or polyamine is added to the oil-in-water emulsion through the aqueous phase, maintaining mild agitation throughout. Stirring is continued typically for 30 minutes to 3 hours until the formation of the (non-continuous) matrix is complete. The reaction temperature is generally in the range from about 20° C. to about 60° C. In the situation where approximately equimolar amounts of isocyanate and amino groups are present, the reaction temperature is preferably from about 20° C. to about 40° C., and even more preferably from about 20° C. to about 30° C. In the situation where an excess of isocyanate groups are present, the reaction temperature is preferably from about 30° C. to about 60° C., and even more preferably from about 40° C. to about 50° C. Reaction times in excess of 3 hours combined with temperatures of 60° C. or above are not recommended; such conditions have been utilised for the encapsulation of suspensions of water-insoluble compounds (US 2003/0119675 and JP 2000247821) but it has been found that such conditions are not suitable for the formation of the microcapsules of this invention, as they result in poor encapsulation efficiency (the water-solubility of the active compounds increases with increasing temperature, resulting in excessive quantities of the active compound transferring into the aqueous phase).

To form a (non-continuous) matrix, many other microencapsulation techniques are possible, including:

(i) Preparation of a microcapsule in which a monomer is present in the disperse phase and is caused to undergo polymerisation to form the (non-continuous) matrix. Such monomers should be essentially water immiscible and typically comprise a vinyl reactive monomer, for example, C1-C16 alkyl esters of acrylic and methacrylic acid such as ethyl hexyl acrylate and ethyl hexyl methacrylate. Crosslinking may also be introduced by choice of an appropriate acrylate or methacrylate monomer such as glycidyl methacrylate;

(ii) preparation of a microcapsule in which the solid water-soluble, biologically active compound is dispersed within a liquid in which a reagent is dissolved, and in which the liquid and reagent are caused to react to form the (non-continuous) matrix. Such effects may be achieved by two reactive species, as are required to produce a polyurethane. These include organic liquid soluble polyols to react with a suitable isocyanate. When the isocyanate reactive species has sufficient functionality, the polyol may contain just one polymerisable hydroxyl group. Many chemistries qualify including alcohols and surfactant products derived from alkoxylation processes (including ethylene oxide, propylene oxide and butylene oxide or mixtures thereof. When the isocyanate has less functionality or where high degrees of cross linking are desired within the (non-continuous) matrix, the polyol component may comprise more than one polymerisable OH (hydroxyl) functional compounds, suitably comprising two or more hydroxyl groups, per molecule on average. The polymerisable, hydroxyl functional compounds may be aliphatic and/or aromatic. The polymerizable, hydroxyl functional compounds may be straight, cyclical, fused, and/or branched. Particular polymerizable hydroxyl functional compounds include at least one diol, at least one triol, and/or at least one tetrol. Any of these polyol compounds may be monomeric, oligomeric, and/or polymeric as desired. If oligomeric and/or polymeric, the polyol(s) may be selected from one or more hydroxyl functional polyethers, polyesters, polyurethanes, polyacrylics, epoxy resins, polyamides, polyamines, polyureas, polysulfones, combinations of these, or the like. Polyether polyols such as the polyalkylene ether and polyester polyols are also suitable and these are commercially available at relatively low cost and are hydrolytically stable.

Suitable polyalkylene ether polyols include poly(alkylene oxide) polymers which are essentially water immiscible and organic soluble, such as poly(ethylene oxide) and poly(propylene oxide) polymers and copolymers with terminal hydroxyl groups derived from polyhydric compounds, including diols and triols; for example, ethylene glycol, propylene glycol, 1,3-butane diol, 1,4-butane diol, 1,6-hexanediol, neopentyl glycol, diethylene glycol, dipropylene glycol, pentaerythritol, glycerol, diglycerol, trimethylol propane and similar low molecular weight polyols. Suitable commercially available polyether polyols include those sold under the trade name Voranole® (The Dow Chemical Company).

The polyester polyols which are suitable in accordance with the invention include known polycondensates of organic dihydroxy and optionally polyhydroxy (trihydroxy, tetrahydroxy) compounds and dicarboxylic and also optionally polycarboxylic (tricarboxylic, tetracarboxylic) acids or hydroxycarboxylic acids or lactones. Instead of the free polycarboxylic acids it is also possible to use the corresponding polycarboxylic anhydrides or corresponding polycarboxylic esters of lower alcohols to prepare the polyesters such as, for example, phthalic anhydride. Examples of suitable diols are ethylene glycol, 1,2-butanediol, diethylene glycol, triethylene glycol, polyalkylene glycols, such as polyethylene glycol, and also 1,2- and 1,3-propanediol, 1,4-butanediol, 1,6-hexanediol, neopentyl glycol or neopentyl glycol hydroxypivalate. Examples of polyols having 3 or more hydroxyl groups in the molecule, which may be used additionally, if desired, include trimethylolpropane, trimethylolethane, glycerol, erythritol, pentaerythritol, di-trimethylolpropane, dipentaerythritol, trimethylol-benzene and trishydroxyethyl isocyanurate.

A particularly suitable class of polyols useful in the compositions, coatings and methods of the invention are the water insoluble phthalic anhydride based polyester-ether polyols which are described, for example, in U.S. Pat. No. 6,855,844 which is incorporated by reference herein. Suitable commercially available phthalic anhydride based polyester-ether polyols include the "Stepanpols"® (Stepan Company).

Other relatively simple feedstocks include natural products that contain reactive hydroxyl groups such as castor oil. These systems require the addition of a suitable catalyst that may be added as needed to any of the phases in the formulation. Suitable catalysts are well known in the art but include organometal catalysts such as dibutyl tin dilaurate and tertiary amines such as triethylamine and triisopropanolamine; and (iii) preparation of a microcapsule wherein a (non-continuous) matrix-forming compound is caused to separate within the microcapsule by removal of a volatile solvent for that compound. This may be achieved by firstly preparing a dispersion of the solid water-soluble biologically active compound in a solution of a water insoluble (non-continuous) matrix forming polymer and a water immiscible volatile solvent for that water insoluble (non-continuous) matrix forming polymer, secondly forming an emulsion of this water-immiscible mixture in water, stabilising that emulsion by an appropriate technique and then removing the volatile solvent by a suitable evaporation process, yielding a dispersion in water of microcapsules containing the water-soluble biologically active compound distributed throughout a (non-continuous) matrix of the water insoluble polymer. The stabilisation of the intermediate emulsion may be achieved by any suitable microencapsulation process, such as an interfacial polycondensation by the routes well known and outlined above but also by such routes as identified in U.S. Pat. No. 5,460,817, where the technology is identified as being useful for water insoluble (and oil soluble) biologically active compounds such as chlorpyrifos and trifluralin but does not refer to utility for dispersions in an oil or polymer of a solid water-soluble biologically active compound. Suitably the matrix is a polymer which is a polyurea, a polyamide or a polyurethane or is a mixture of two or more of these polymers; more suitably the matrix is a polyurea.

In the preparation of such microcapsules, it is naturally assumed that the substantially water immiscible liquid used for the preparation of the dispersion of the solid water-soluble biologically active compound will be essentially retained within the microcapsule (unless removed deliberately by evaporation as discussed above). Undesired loss of solvent may alter (and destabilise) the capsule structure and release characteristics. One preferred embodiment of the capsule is where the water-immiscible liquid does not migrate into the water phase and, moreover, is involatile such that drying operations on the aqueous compositions do not result in solvent loss and thus alteration of the desired capsule composition.

For the purposes of this invention, the term water-soluble as used when referring to the biologically active compound to be encapsulated is defined as a water-solubility in the range of 0.1-100 g/l, preferably in the range 0.5-50 g/l, at 20° C. This may be any such compound from the group comprising pharmaceuticals and agrochemicals such as insecticides, herbicides, fungicides, acaricides, rodenticides, molluscicides and plant growth regulators.

Suitable herbicides include 2,3,6-TBA, 2,4-D, 2-chloro-6'-ethyl-N-isopropoxymethylaceto-o-toluidide, acifluorfen, alachlor, ametryn, amicarbazone, amidosulfuron, asulam, azimsulfuron, benazolin, benfuresate, bensulfuron-methyl, bentazone, bromacil, carbetamide, chloridazon, chlorimuron-ethyl, chlorsulfuron, cinosulfuron, clomazone, cloransulam-methyl, cyanizine, cyclosulfamuron, dicamba, dichlorprop, dichlorprop-P, diflufenzopyr, dimethachlor, dimethipin, diphenamid, ethametsulfuron-methyl, ethoxysulfuron, fenoxaprop-P, flazasulfuron, florasulam, flucetosulfuron, flumioxazin, fluometuron, flupyrsulfuron-methylsodium, fluoroxypyr, fomesafen, foramsulfuron, halosulfuron-methyl, haloxyfop-P, imazamethabenz-methyl, imazamox, imazapic, imazapyr, imazethapyr, imazasulfuron, iodosulfuron-methyl-sodium, isouron, MCPA, MCPB, mecoprop, mecoprop-P, mesosulfuron-methyl, mesotrione, metamitron, metazachlor, methyldymron, metosulam, metoxuron, metribuzin, metsulfuron-methyl, monolinuron, naptalam, oxasulfuron, penoxsulam, pethoxamid, primisulfuron-methyl, prometon, propachlor, propanil, propham, propoxycarbazone-sodium, prosulfuron, pyroxyfen, quinmerac, rimsulfuron, simetryn, sulcotrion, sulfentrazone, sulfometuron-methyl, sulfosulfuron, tebuthiuron, tepraloxydim, terbacil, terbumeton, thifensulfuron-methyl, tralkoxydim, triasulfuron, tribenuron-methyl, triclopyr and trisulfuron-methyl.

Suitable fungicides include 2-phenylphenol, azaconazole, azoxystrobin, carboxin, cymoxanil, cyproconazole, dodemorph acetate, dodine, epoxyconazole, etridiazole, fenfuram, ferimzone, flusilazole, flutriafol, fuberidazole, furalaxyl, furametpyr, imazalil, metalaxyl, methasulfocarb, metominostrobin, myclobutanil, ofurace, oxadixyl, oxycarboxin, phenylmercury acetate, propiconazole, prothioconazole, pyrimethanil, pyroquilon, tetraconazole, thiabendazole and tricyclazole.

More suitable fungicides include 2-phenylphenol, azaconazole, carboxin, cymoxanil, dodemorph acetate, dodine, etridiazole, fenfuram, ferimzone, flusilazole, flutriafol, fuberidazole, furalaxyl, furametpyr, imazalil, metalaxyl, methasulfocarb, metominostrobin, myclobutanil, ofurace, oxadixyl, oxycarboxin, phenylmercury acetate, prothioconazole, pyrimethanil, pyroquilon, tetraconazole, thiabendazole and tricyclazole.

Suitable insecticides include abamectin, acetamiprid, aldicarb, azadirachtin, azamethiphos, bendiocarb, carbaryl, carbofuran, clothianidin, cryolite, dazomet, dimethylvinphos, DNOC, emamectin benzoate, ethiofencarb, ethylene dibromide, fenamiphos, fenobucarb, fipronil, flonicamid, imidacloprid, isoprocarb, lufenuron, methidathion, methyl isothiocyanate, metlocarb, pirimicarb, propoxur, pymetrozine, pyridaphenthion, chlioranthraniliprole (Renaxapyr™), sabadilla, spinosad, sulcofuron-sodium, thiacloprid, thiamethoxam, thiofanox, triazamate, XMC and xylylcarb.

More suitable insecticides include acetamiprid, aldicarb, azadirachtin, azamethiphos, bendiocarb, carbaryl, carbofuran, clothianidin, cryolite, dazomet, dimethylvinphos, DNOC, ethiofencarb, ethylene dibromide, fenamiphos, fenobucarb, fipronil, flonicamid, imidacloprid, isoprocarb, methidathion, methyl isothiocyanate, metlocarb, pirimicarb, propoxur, pymetrozine, pyridaphenthion, sabadilla, spinosad, sulcofuron-sodium, thiacloprid, thiamethoxam, thiofanox, triazamate, XMC and xylylcarb.

Suitable rodenticides include chloralose, chlorophacinone, coumatetralyl and strychnine.

Suitable molluscicides include metaldehyde and niclosamide.

Suitable plant growth regulators include 1-naphthylacetic acid, 4-indol-3-ylbutyric acid, ancymidol, cloxyfonac, ethychlozate, flurprimidol, gibberellic acid, indol-3-ylacetic acid, maleic hydrazide, mefluidide, prohexadione-calcium and trinexapac-ethyl.

Particularly suitable insecticides are the neonicotinoids such as acetamiprid, clothianidin, imidacloprid, thiacloprid and thiamethoxam. An especially suitable insecticide is thiamethoxam.

In a further aspect, the present invention provides use of a product to combat or control an agricultural pest which comprises applying to the pest or to a locus of the pest, a pesticidally effective amount of the product. The pests may include [fungal] diseases, insects and weeds. Suitably the pest is a termite.

The concentration of the solid water-soluble biologically active compound is suitably from 0.1-70% [more suitably 0.1-65%] by weight of the microcapsule.

For those cases in which the solid water-soluble biologically active compound is suspended in a substantially water-immiscible liquid, said liquid may be any liquid which does not dissolve the compound to any appreciable extent but is a sufficiently good solvent to dissolve the reagents or prepolymers used to form the (non-continuous) matrix. Suitably the water-solubility of the liquid under ambient conditions [typically 20° C.] is approximately 5000 ppm by weight or less.

Suitable examples of such liquids are aromatic organic compounds such as xylenes or naphthalenes, eg. Solvesso® 200; aliphatic organic compounds such as alkyl esters, eg. Exxate® 700-Exxate® 1000, Prifer® 6813; paraffinic compounds, eg. the Norpar® & Isopar® ranges of solvents; alkyl phthalates, such as diethyl phthalate, dibutylphthalate and dioctylphthalate; alcohols, such as isopropyl alcohol; ketones, such as acetophenone and cyclohexanone; mineral oils, eg. Cropspray® 7N or 11N; vegetable or seed oils, such as rapeseed oil; and alkylated seed oils. The liquid may be a mixture of more than one compound.

Furthermore the liquid in which the biologically active compound is suspended may in itself be or comprise a second biologically active compound.

The phase volumes of the disperse organic phase and the continuous aqueous phase may be varied within a wide range; typically the organic phase is present at 5 to 70% by weight; suitably from 15 to 70% by weight; and more suitably from 15 to 50% by weight based on the entire formulation.

The liquid suitably contains a dispersant. The exact choice of dispersant(s) will depend on the choice of solid and the liquid but particularly suitable dispersants are those which act by steric hindrance and are active only at the solid/organic liquid interface and do not act as emulsifying agents. Such dispersants are suitably made up of (i) a polymeric chain having a strong affinity for the liquid and (ii) a group which will adsorb strongly to the solid.

Examples of dispersants which may be used in microcapsules containing a solid biologically active compound suspended in a liquid [and which are generally polymeric] are given in WO 95/13698, and include products available under the tradenames Hypermer®, Atlox®, Agrimer® and Solsperse®.

In general, the range of dispersant concentration used is from about 0.01 to about 10% by weight based on the organic phase, but higher concentrations may also be used.

For the successful encapsulation of suspensions of solid water-soluble biologically active compounds according to the present invention the choice of the liquid/dispersant combination within the microcapsules is particularly critical. Suitable systems include Solvesso® 200 and Solsperse® 17000; rapeseed oil and Solsperse® 17000; a Norpar® 15/Prifer® 6813 mixture with Z190-165™; and Cropspray® 7N or 11N with one or more dispersants selected from Atlox® 4912, Atlox® LP1, Agrimer® AL22 and Agrimer® AL30. Such combinations are particularly suitable when the biologically active compound is thiamethoxam.

In general, the surfactant or surfactants in the aqueous phase of the microcapsule suspension are selected from anionic, cationic and non-ionic surfactants with an HLB range from about 10 to about 16 that is high enough to form a stable oil-in-water emulsion; non-ionic surfactants are particularly suitable. If more than one surfactant is used, the individual surfactants may have HLB values lower than 10 or higher than 16. However, when combined together the overall HLB value of the surfactants may be in the range 10-16. Suitable surfactants include polyethylene glycol ethers of linear alcohols, ethoxylated nonylphenols, tristyrylphenol ethoxylates, block copolymers of propylene oxide and ethylene oxide, and polyvinyl alcohols. Polyvinyl alcohols are particularly suitable.

In general, the range of surfactant concentration in the process is from about 0.01 to about 10% by weight, based on the aqueous phase, but higher concentrations of surfactant may also be used.

Additionally, a protective colloid may also be present in the aqueous phase. This must adsorb strongly onto the surface of the oil droplets. Suitable protective colloids include polyalkylates, methyl cellulose, polyvinyl alcohols, mixtures of polyvinyl alcohols and gum arabic, and polyacrylamides. Polyvinyl alcohols are particularly suitable.

There should be sufficient colloid present to afford complete coverage of the surfaces of all the droplets of the organic liquid. The amount of protective colloid employed will depend on various factors, such as molecular weight and compatibility. The protective colloid may be added to the aqueous phase prior to the addition of the organic phase, or can be added to the overall system after the addition of the organic phase or the dispersion of it. The protective colloid is generally present in the aqueous phase in an amount of from about 0.1 to about 10% by weight of the aqueous phase.

Where separate emulsifiers and colloid stabilisers are used in the aqueous phase, the emulsifier should not displace the protective colloid from the surface of the droplets of the organic liquid.

In the situation in which the microcapsules are prepared via an interfacial polycondensation reaction, the organic phase and/or the aqueous phase contains one or more materials which may react to form the polymer (non-continuous) matrix. In one preferred embodiment, the organic phase contains at least one diisocyanate and/or polyisocyanate, whilst the aqueous phase contains at least one diamine and/or polyamine.

Any diisocyanate or polyisocyanate, or mixtures thereof, may be employed, provided that it is soluble in the liquid chosen for the organic phase. Where aromatic liquids are used, aromatic isocyanates such as isomers of tolylene diisocyanate, isomers and derivatives of phenylene diisocyanate, isomers and derivatives of biphenylene diisocyanates, and/or polymethylenepolyphenyleneisocyanates (PMPPI) are suitable. Where aliphatic liquids are used, aliphatic isocyanates are suitable, for example aliphatic acyclic isocyanates such as hexamethylenediisocyanate (HMDI), cyclic aliphatic isocyanates such as isophoronediisocyanate (IPDI) or 4,4'methylenebis(cyclohexyl isocyanate), and/or trimers of HMDI or IPDI and the like. Polymeric polyisocyanates, biurets, blocked polyisocyanates, and mixtures of polyisocyanates with melting point modifiers may also be used. MDI is a particularly preferred polyisocyanate. Should other properties be desired from the isocyanate such as increased flexibility, then pegylated derivatives may be employed wherein part of the isocyanate is reacted with a suitable polyol. Such techniques and chemistries are well known in the art.

The concentration of the isocyanate(s), and the ratio(s) where more than one isocyanate is used, is/are chosen so as to obtain the desired release rate profile for the particular end application. The concentration of the isocyanate(s) must also be high enough to form a (non-continuous) matrix dispersed throughout the microcapsules. In general, the isocyanate(s) will comprise from about 5 to about 75%, more suitably from about 7 to about 30%, even more suitably from about 10 to about 25% and most suitably from about 10 to about 20%, by weight of the microcapsule.

The diamine or polyamine, or mixtures thereof, may be any such compound(s) which is/are soluble in the aqueous phase. Aliphatic or alicyclic primary or secondary diamines or polyamines are very suitable, such as ethylene-1,2-diamine, diethylenetriamine, triethylenetetramine, bis-(3-aminopropyl)-amine, bis-(2-methylaminoethyl)-methylamine, 1,4-diaminocyclohexane, 3-amino-1-methylaminopropane, N-methyl-bis-(3-aminopropyl)amine, 1,4-diamino-n-butane, 1,6-diamino-n-hexane and tetraethylenepentamine. Polyethyleneimines are also suitable.

The molar ratio of amine moieties to isocyanate moieties may be varied from about 0.1:1 to about 1.5:1. Suitably either (i) approximately equimolar concentrations of amine and isocyanate moieties are employed, with the molar ratio of amine to isocyanate moieties ranging from about 0.8:1 to about 1.3:1, in which case the wall formation reaction is suitably carried out at a temperature from about 20° C. to about 40° C., even more preferably from about 20° C. to about 30° C.; or (ii) a significant excess of isocyanate is present, with the ratio of amine to isocyanate moieties ranging from about 0.1:1 to about 0.35:1, in which case the wall formation reaction is preferably carried out at a temperature from about 30° C. to about 60° C., even more preferably from about 40° C. to about 50° C. In case (i), the reaction between approximately equimolar concentrations of amine and isocyanate moieties results in the formation of a polyurea (non-continuous) matrix which is distributed throughout the microcapsules. In case (ii), an initial reaction occurs between some of the isocyanate moieties and the amine moieties to fix a shell around the outside of the emulsion droplets, followed by hydrolysis and further reaction of the excess isocyanate moieties to form a (non-continuous) matrix which is distributed throughout the resultant microcapsules.

Other wall chemistries may be used, for example polyurethanes and polyamides, by appropriate selection of wall forming components. Suitable glycols for addition through the aqueous phase include those taught above and which are water soluble. These may also include simple polyhydroxylic glycols, for example, suitable diols are ethylene glycol, 1,2-butanediol, diethylene glycol, triethylene glycol, polyalkylene glycols, such as polyethylene glycol, and also 1,2- and 1,3-propanediol, 1,4-butanediol, 1,6-hexanediol, neopentyl glycol or neopentyl glycol hydroxypivalate. Examples of polyols having 3 or more hydroxyl groups in the molecule, which may be used additionally, if desired, include trimethylolpropane, trimethylolethane, glycerol, erythritol, pentaerythritol, di-trimethylolpropane, dipentaerythritol, trimethylol-benzene and trishydroxyethyl isocyanurate. Higher functionality may be employed by use of the various sugars such as fructose, dextrose, glucose and derivatives thereof. It is noted that glycols with suitable oil solubility characteristics may be introduced into the oil phase as part of the dispersion of the solid water-soluble biologically active compound whereby they can contribute not only to capsule wall formation but also (as indicated earlier) to (non-continuous) matrix formation. Mixtures of water soluble and oil soluble reactive hydroxyl containing compounds are also contemplated. Polyamides may be produced in a similar manner by selection of an appropriate acid feedstock (such as sebacoyl chloride). Mixtures, in any ratio, of polyureas, polyurethanes and polyamides are also part of the present invention. Therefore suitably the polymeric shell is a polymer which is a polyurea, a polyamide or a polyurethane or is a mixture of two or more of these polymers; more suitably the polymeric shell is a polyurea.

In a similar manner, oil soluble amines may be contemplated as being added to the oil phase prior to preparation of the aqueous dispersion and thereafter a suitable water dispersible isocyanate reactant may be added to complete the interfacial reaction.

By selection of microcapsule size, isocyanate chemistry and concentration, amine identity and the ratio of different isocyanate monomers and/or amines when more than one isocyanate monomer and/or amine is present, the release rate of the solid water-soluble biologically active compound can be varied from a half-life [T50; the time taken for 50% of the active ingredient to be lost from the capsule (i.e. released)] value of a few hours up to several months or years. It is surprising that such a wide range of release rates is achievable for a water-soluble biologically active compound, and it is particularly unexpected that extremely slow release rates into an aqueous sink are obtained.

Furthermore, mixtures of microcapsules with different release rates may be combined in a single formulation, to provide a tailored release profile.

The capsule compositions, as produced, will be dispersions in water. These microcapsules may be post-formulated, to stabilise them for long term shelf life storage, with anti-settling agents, which include water-soluble polysaccharides such as xanthan gum, water-insoluble polysaccharides such as microcrystalline cellulose and structured clays such as bentonites. Microcrystalline cellulose is a particularly suitable anti-settling agent.

Furthermore, it is possible to add additional biologically active compounds to the aqueous phase, either as solids, emulsions (either as an emulsion of a compound that is liquid at ambient temperature or as an emulsion of a solution of a biologically active compound in a suitable essentially water immiscible solvent) or as a solution in water or mixtures of the above. The biologically active compound added directly to the external aqueous phase may be the same compound as within the microcapsule.

Suitably the agrochemical in the aqueous phase has a water-solubility in the range of 0.1 to 100 g/l at 20° C.; more suitably the agrochemical in the aqueous phase is a neonicitinoid insecticide; even more suitably it is acetamiprid, clothianidin, imidacloprid, thiacloprid or thiamethoxam; and most suitably it is thiamethoxam.

Where an additional biologically active compound is present in the aqueous phase, the concentration of this compound may be varied within a relatively wide range. Generally the concentration of this compound will be between 0 and 50% by weight, based on the total aqueous phase.

Furthermore, it is possible to dry such water based compositions. This can be achieved by concentration of the water based composition (e.g. sedimentation, centrifugation) followed by a suitable drying technique such as drum drying. It may also be achieved by techniques such as spray-drying [including fluid bed agglomeration techniques and similar granulation processes] or, if the compounds are heat sensitive, freeze drying or atmospheric freeze drying. Spray drying techniques are preferred as they are fast and may conveniently be applied to dispersions such as the microcapsules of this invention. Production of dry product from a water based dispersion usually requires the addition of further inert components to protect the integrity of the capsules during the drying stage, or during storage and also to allow easy complete re-dispersion of the dry product back into water for application. Such inerts include, but are not limited to, essentially water soluble film-forming agents such as polyvinyl alcohols, polyvinylpyrrolidones and polyacrylic acids. Other ingredients may include surfactants, dispersants, sugars, lignosulfonates, disintegrants such as cross-linked polyvinylpyrrolidones and maltodextrins.

The dried products moreover, may contain other biologically active agents that are not encapsulated as described above for the water-soluble biologically active agents.

It is also possible to use a dried product directly without dilution into water. Such use may be as a granular product in rice cultivation, for use on cultivated turf and also as a feedstock for blending into fertiliser mixtures for subsequent application to soil, turf or other targets such as rice.

Suitably the dry product is granular.

Suitably the dry product is water-dispersible.

The wide range of release rates achievable with the technology of the present invention allows exploitation in several applications, including traditional crop protection outlets both as a foliar or a soil applied product, for use on cultivated turf, as a seed treatment and numerous other applications such as protection against termites and as a long-lasting residual spray for general pest control.

In a still further aspect of the invention there is provided the use of a composition as described herein for the protection of industrial materials [referred to as "materials protection"]. Suitably the industrial material to be protected is selected from the group consisting of: wood; plastic; wood plastic composite; paint; paper; and wallboards. The protection may be in the form of a product that deters, repels or kills an attack of a target, such as in the area of termite protection, or house protection against invasive insect species, a barrier can be places between the article to be protected (eg a building) and the external environment in which the pest species normally resides.

The term "Industrial Material" includes those materials used in construction and the like. For example, Industrial Material may be structural timber, doors, cupboards, storage units, carpets, particularly natural fibre carpets such as wool and hessian, plastics, wood (including engineered wood) and wood plastic composite.

In a particular embodiment the Industrial Material is a coating. "Coating" includes compositions applied to a substrate, for example, paints, stains, varnishes, lacquers, primers, semi-gloss coatings, gloss coatings, flat coatings, topcoats, stain-blocking coatings, penetrating sealers for porous substrates, concrete, marble, elastomeric coatings, mastics, caulks, sealants, board and paneling coatings, transportation coatings, furniture coatings, coil coatings, bridge and tank coatings, surface marking paints, leather coatings and treatments, floor care coatings, paper coatings, personal care coatings [such as for hair, skin or nails], woven and non-woven fabric coatings, pigment printing pastes, adhesive coatings [such as, for example, pressure sensitive adhesives and wet- or dry-laminating adhesives] and plaster.

Suitably "coating" means paint, varnish, stain, lacquer or plaster; more suitably "coating" is a lacquer or alternatively "coating" may mean paint. Paint may comprise, for example, a film former and a carrier (which carrier can be water and/or an organic solvent) and optionally a pigment.

In addition to this, "Industrial Material" includes adhesives, sealants, joining materials, joints and insulation material.

"Wood" is to be understood to include wood and wood products, for example: derived timber products, lumber, plywood, chipboard, flakeboard, laminated beams, oriented strandboard, hardboard, particle-board, tropical wood, structural timber, wooden beams, railway sleepers, components of bridges, jetties, vehicles made of wood, boxes, pallets, containers, telegraph-poles, wooden fences, wooden lagging, windows and doors made of wood, plywood, chipboard, joinery, or wooden products which are used, quite generally, for building houses or decks, in building joinery or wood products that are generally used in house-building including engineered wood, construction and carpentry.

"Industrial Material" also includes wallboards such as gypsum based wallboards.

In a still further aspect of the invention there is provided "Industrial Materials" comprising a composition as herein described. In a particular embodiment said Industrial materials are selected from the group consisting of: wood; wood plastic composite; paint; paper; and wallboards. In a particular embodiment said Industrial materials comprise wood.

Examples of ways in which an Industrial Material can be treated with a product according to the invention are: by including said product in the Industrial Material itself, absorbing, impregnating, treating (in closed pressure or vacuum systems) said material with said fungicide, dipping or soaking the building material, or coating the building material for example by curtain coating, roller, brush, spray, atomisation, dusting, scattering or pouring application.

The use of slow releasing microcapsules allows for an extended period of biological control compared to non-encapsulated formulations, and for soil applied products the extent of leaching may also be reduced by the use of such microcapsules; the latter is particularly relevant for the active compounds disclosed within this invention, whereby their substantial water solubility renders them prone to leaching when applied in an non-encapsulated form. In the particular embodiment where the microcapsules are suspended in an aqueous medium comprising a suspension of non-encapsulated biologically active compound, both rapid knockdown activity and an extended period of biological control may be achieved, particularly for insecticides. Other utilities include incorporation of such products into materials where a slow release of a water soluble material is desired, such as for treatment of water bodies and addition to centre pivot irrigation systems where high volumes of water rapidly leach active materials.

The microcapsule suspensions thus produced may be utilized in the normal fashion of such products, i.e. by packaging the suspension and ultimately transferring the suspension into a spray tank or other spray equipment, in which it is mixed with water to form a sprayable suspension. A range of application techniques may be utilised for the soil application of such microcapsules, including pre-planting and post-planting applications either as a dilute spray or as a more concentrated drench, including direct application into the planting hole. Application may also be made to seedling trays etc. prior to transplant. For termite protection, the microcapsules of this invention may be applied as a soil drench underneath the foundations, as a perimeter 'trench and treat' barrier around the outside of the foundations, or applied directly onto concrete. Alternatively, the suspension of microcapsules may be converted into a dry microcapsule product by spray drying or other known techniques and the resulting material packaged in dry form.

It will be appreciated that there are many aspects to the present invention. In one aspect it relates to a microcapsule formulation in which microcapsules comprise a solid water-soluble, biologically active compound dispersed in a (non-continuous) matrix which is at least partially solid and which is distributed throughout the microcapsules. In particular it relates to a product comprising microcapsules which themselves comprise (a) a polymeric shell; and
(b) a core which comprises (i) a solid agrochemical dispersed in a matrix and (ii) a water-immiscible liquid characterised in that the matrix is distributed non-continuously throughout the water-immiscible liquid.

Further aspects and preferences are given below.

A microcapsule formulation in which microcapsules comprise a solid water-soluble, biologically active compound dispersed in a (non-continuous) matrix which is at least partially solid and which is distributed throughout the microcapsules, in which the microcapsules are suspended in an aqueous phase during their formation.

A microcapsule formulation as described above wherein the water soluble biologically active compound is a solid at ambient temperature and is dispersed in an organic non-solvent within the capsules.

A microcapsule formulation as described above and a process as described above for making it in which a monomer is present in the disperse phase and is caused to undergo polymerisation to form the (non-continuous) matrix.

A microcapsule formulation as described above wherein a water immiscible liquid is a vinyl containing reactive monomer.

A microcapsule formulation as described above and a process as described above for making it in which the water-soluble, biologically active compound is dispersed within a liquid in which a reagent is dissolved, and in which the liquid and reagent are caused to react to form the (non-continuous) matrix.

A microcapsule formulation as described above wherein a water immiscible liquid is a reactant with a second reactive species by which a (non-continuous) matrix is formed.

A microcapsule formulation as described above in which the water-soluble, biologically active compound is dispersed within a substantially water-immiscible liquid which is retained within the microcapsule.

A microcapsule formulation as described above in which the substantially water-immiscible liquid is or comprises a second biologically active compound.

A microcapsule formulation as described above in which one or more biologically active compounds is/are present in the continuous aqueous phase [either as a solid dispersion, a liquid dispersion or as a solution in the aqueous phase].

A microcapsule formulation as described above in which the biologically active compound which is present in the continuous aqueous phase is the same water-soluble biologically active compound as the one which is dispersed in the microcapsules.

A microcapsule formulation as described above in which the water-soluble, biologically active compound is a pesticide.

A microcapsule formulation as described above in which the pesticide is thiamethoxam.

The use of a microcapsule formulation as described above to control the release rate of a pesticide thereby providing an extended period of biological control.

The use of a microcapsule formulation as described above to control the release rate of a pesticide thereby providing a reduction in leaching of the pesticide.

A microcapsule formulation as described above wherein the formulation is water based (capsules dispersed in water).

A microcapsule formulation as described above where the formulation is a dry product, produced by a drying process such as spray drying or freeze drying or by a suitable concentration procedure and final drying.

A microcapsule formulation as described above where a (non-continuous) matrix-forming compound (suitably a polymer) is caused to separate within the microcapsule by removal of a volatile solvent for that compound.

The use of a microcapsule formulation as described above to improve safety of a biogiclly active compound either to the manufacturer, user or the environment.

A process for forming a microcapsule formulation as described above in which the (non-continuous) matrix is prepared either before the capsule, during capsule preparation or after capsule preparation.

A process for forming a microcapsule formulation as described above in which the (non-continuous) matrix is formed by an interfacial polycondensation reaction.

A process as described above in which at least one reagent for the polycondensation reaction is present in the dispersed [organic] phase and at least one reagent for the polycondensation reaction is present in the continuous [aqueous] phase.

A process as described above in which the reagents for the polycondensation reaction are only present in the dispersed phase.

The following examples are given by way of illustration and not by way of limitation of the invention, in which many capsule samples are characterised by their VMD [Volume Median Diameter].

EXAMPLES 1a-1w

The following examples demonstrate that a suspension of thiamethoxam particles can be successfully encapsulated within polyurea microcapsules, the (non-continuous) matrix within the capsules being formed at ambient temperature from the reaction between essentially equimolar concentrations of isocyanate and amine moieties. Such formulations are not trivial to prepare successfully due to the high water-solubility of thiamethoxam (4.1 g/l at 20° C.) which means there is a tendency for the particles of thiamethoxam to migrate into the aqueous phase during the emulsification process, and/or during the formation of the (non-continuous) matrix.

Thiamethoxam was encapsulated using the following process according to the recipes given in Table 1. An organic phase was prepared by the addition of one or more isocyanates to a finely ground suspension of thiamethoxam in a substantially water immiscible solvent. This was emulsified into an aqueous solution of polyvinylalcohol to obtain the desired particle size. Then a solution of a polyfunctional amine was added, and the wall formation reaction was allowed to proceed at ambient temperature, maintaining gentle agitation throughout. Finally, postformulation (adjustment to neutral pH and addition of antisettling agents) was carried out as required.

Rapeseed oil (from *Brassica rapa*) was sourced from Fluka.
Solvesso® 200 is an aromatic hydrocarbon solvent supplied by Exxon.
Cropspray® 7N is a mineral oil supplied by Sun Oil Company.
Norpar® 15 and Prifer® 6813 are paraffinic solvents supplied by Exxon.
Solsperse® 17000 is a polymeric dispersant supplied by Lubrizol.
Z190-165™ is a polymeric dispersant supplied by Uniqema.
Agrimer® AL22 is an alkylated vinylpyrrolidone copolymer supplied by ISP.
Desmodur® Z4470 is the trimer of isophoronediisocyanate supplied by Bayer as a 70% solution in naphtha 100.
Desmodur® W is 4,4'-methylenebis(cyclohexyl isocyanate) supplied by Bayer.
TDI is an 80:20 mixture of tolylene 2,4- & 2,6-diisocyanate supplied by Sigma Aldrich.
Suprasec® 5025 (polymethylene polyphenylene isocyanate) is supplied by Huntsman.
Gohsenol® GL03, GL05 and GM14-L are polyvinylalcohols supplied by Nippon Gohsei.
Polyethyleneimine (Mn~600 [Mn is number average molecular weight], M. Wt.~800 Daltons) is supplied by Aldrich.
Avicel® CL611 is a microcrystalline cellulose supplied by FMC.
Kelzan® is a xanthan gum supplied by CP Kelco.
After sample preparation, each sample was characterised by measuring its VMD.

TABLE 1

| Component (g/l) | 1a | 1b | 1c | 1d | 1e | 1f | 1g | 1h |
|---|---|---|---|---|---|---|---|---|
| Thiamethoxam | 75 | 75 | 75 | 75 | 75 | 75 | 180 | 183.4 |
| Solsperse 17000 | 7.5 | 7.5 | 7.5 | 7.5 | 7.5 | 7.5 | 18 | 16.7 |
| Rapeseed oil | 86.3 | 86.3 | 86.3 | 86.3 | 78.2 | 78.2 | 205.7 | 175 |
| Desmodur Z4470 SN | 56.1 | 56.1 | 56.1 | 56.1 | 64.3 | 64.3 | 121.6 | 125 |
| Gohsenol GL03 | 33.8 | 33.8 | 33.8 | 33.8 | 33.8 | 33.8 | 78.1 | 75 |
| Diethylenetriamine | 5.6 | 5.6 | 5.6 | 5.6 | 6.4 | 6.4 | 13.1 | 12.5 |
| Avicel CL611 | 10 | 10 | 10 | 10 | 10 | 10 | 10 | 10 |
| Water | To 1 litre | To 1 litre | To 1 litre | To 1 litre | To 1 litre | To 1 litre | To 1 litre | To 1 litre |
| VMD/(μm) | 7.9 | 9.1 | 13.1 | 16.4 | 8.5 | 10.3 | 13.78 | 16.38 |

| Component (g/l) | 1i | 1j | 1k | 1l | 1m |
|---|---|---|---|---|---|
| Thiamethoxam | 104 | 75 | 75 | 75 | 75 |
| Solsperse 17000 | 5.4 | 6.3 | 6.3 | 6.3 | 6.3 |
| Rapeseed oil | 69 | — | — | — | — |
| Solvesso 200 | — | 91.3 | 91.3 | 91.3 | 93.5 |
| Desmodur Z4470 SN | 69 | — | — | — | — |
| Suprasec 5025 | — | 30.9 | 31.0 | 31.0 | 19.5 |
| Gohsenol GL03 | 48.5 | — | — | — | — |
| Gohsenol GL05 | — | 21.9 | 15.6 | 15.6 | 14.7 |
| Diethylenetriamine | 7.0 | — | — | — | — |
| 1,6-diamino-n-hexane | — | 14.5 | — | — | — |
| Ethylene-1,2-diamine | — | — | 7.6 | — | — |
| Tetraethylenepentamine | — | — | — | 9.4 | 6 |
| Avicel CL611 | 8.5 | 10 | 10 | 15 | 8 |
| Kelzan | — | — | — | — | 2 |

TABLE 1-continued

| Water | To 1 litre | To 1 litre | To 1 litre | To 1 litre | To 1 litre |
|---|---|---|---|---|---|
| VMD/(μm) | 11 | 6.6 | 13.2 | 10.8 | 14.1 |

| Component (g/l) | 1n | 1o | 1p | 1q | 1r | 1s | 1t | 1u | 1v | 1w |
|---|---|---|---|---|---|---|---|---|---|---|
| Thiamethoxam | 75 | 75 | 75 | 75 | 75 | 120 | 120 | 120 | 120 | 75 |
| Z190-165 | 18.8 | — | — | — | — | — | — | — | — | — |
| Agrimer AL22 | — | 7.5 | 7.5 | 7.5 | 7.5 | 12 | 12 | 12 | 12 | 7.5 |
| Prifer 6813 | 27.5 | — | — | — | — | — | — | — | — | — |
| Norpar 15 | 27.5 | — | — | — | — | — | — | — | — | — |
| Cropspray 7N | — | 67.5 | 67.5 | 67.5 | 67.5 | 108 | 108 | 108 | 108 | 67.5 |
| Desmodur Z4470 SN | 38.2 | — | — | — | — | — | — | — | — | — |
| Desmodur W | — | 26.5 | 12.2 | — | — | 60 | — | 102 | 42.3 | 16.7 |
| TDI | — | — | — | 26.5 | 26.5 | — | 26.7 | — | — | — |
| Gohsenol GL03 | 16 | — | — | — | — | — | — | — | — | — |
| Gohsenol GL05 | — | 20 | 20 | 20 | 20 | 37.5 | 32.1 | 28.9 | 32.1 | 20.1 |
| Gohsenol GM14-L | — | 6.7 | 6.7 | 6.7 | 6.7 | 12.5 | 10.7 | 9.7 | 10.7 | 13.4 |
| Diethylenetriamine | 2.7 | 3.8 | 3.3 | 11.5 | — | — | — | — | — | 4.8 |
| Tetraethylenepentamine | — | 4.2 | — | — | 11.7 | — | 11.8 | 30.6 | 12.6 | — |
| Polyethyleneimine | — | — | — | — | — | 60.8 | — | — | — | — |
| Avicel CL611 | 10 | 10 | 10 | 10 | 10 | — | 5 | 5 | 5 | 10 |
| Water | To 1 litre | To 1 litre | To 1 litre | To 1 litre | To 1 litre | To 1 litre | To 1 litre | To 1 litre | To 1 litre | To 1 litre |
| VMD/(μm) | 18.8 | 15 | 12 | 8.2 | 16.3 | 9.8 | 11.9 | 9.0 | 13.3 | 102 |

EXAMPLES 2a-2d

The following examples demonstrate that a suspension of thiamethoxam particles can be encapsulated within polyurea microcapsules, the (non-continuous) matrix within the capsules being formed by a combination of isocyanate hydrolysis and self-condensation, and the reaction between isocyanate and amine moieties added through the aqueous phase. In these examples the molar ratio of the externally added amine: isocyanate moieties is significantly lower than 1:1. Such formulations are particularly difficult to prepare successfully due to the elevated temperatures utilised during the formation of the (non-continuous) matrix; it is important that a shell is fixed around the outside of the emulsion droplets via initial reaction between the amine moieties and some of the isocyanate moieties to prevent excessive migration of thiamethoxam particles into the aqueous phase. Thiamethoxam was encapsulated using the following process according to the recipes given in Table 2. An organic phase was prepared by the addition of one or more isocyanates to a finely ground suspension of thiamethoxam in a substantially water immiscible solvent. This was emulsified into an aqueous solution of polyvinylalcohol to obtain the desired particle size. Then a solution of a polyfunctional amine was added, the temperature of the emulsion was raised to 40° C. and this temperature was maintained for 3 hours to allow the wall formation reaction to proceed, maintaining gentle agitation throughout. Finally, post-formulation (adjustment to neutral pH and addition of antisettling agents) was carried out as required.

Each sample was then characterised by measuring its VMD.

TABLE 2

| Component (g/l) | 2a | 2b | 2c | 2d |
|---|---|---|---|---|
| Thiamethoxam | 75 | 75 | 75 | 75 |
| Solsperse 17000 | 6.3 | 6.3 | 6.3 | 6.3 |
| Solvesso 200 | 83.7 | 83.7 | 73.9 | 73.9 |
| TDI | 14.6 | 14.6 | 19.5 | 19.5 |
| Suprasec 5025 | 14.6 | 14.6 | 19.5 | 19.5 |
| Gohsenol GL05 | 14.7 | 14.7 | 14.7 | 14.7 |
| 1,6-diamino-n-hexane | 3.1 | 3.1 | 4.2 | 4.2 |
| Avicel CL611 | 8 | 8 | 8 | 8 |
| Kelzan | 2 | 2 | 2 | 2 |
| Water | To 1 litre | To 1 litre | To 1 litre | To 1 litre |
| VMD/(μm) | 10.5 | 16.2 | 13.0 | 22.8 |

EXAMPLE 3

The following example demonstrates the combination of an encapsulated suspension of thiamethoxam with a suspension of unencapsulated thiamethoxam in the aqueous phase. Microcapsules containing a suspension of thiamethoxam were prepared according to the method detailed in example 1, according to the composition in Table 3. The capsule formulation was characterised by measuring its VMD. The microcapsules were then mixed in various ratios with Cruiser™ 350FS (a suspension concentrate containing 350 g/l thiamethoxam) to give final products with ratios of encapsulated to unencapsulated thiamethoxam of 1:1, 1:2 and 2:1 by weight (examples 3a, 3b and 3c respectively).

TABLE 3

| Component (g/l) | |
|---|---|
| Thiamethoxam | 75 |
| Solsperse 17000 | 7.5 |
| Rapeseed oil | 78.2 |
| Desmodur Z4470 SN | 64.3 |
| Gohsenol GL03 | 33.1 |
| Diethylenetriamine | 6.3 |
| Avicel CL611 | 10 |
| Water | To 1 litre |
| VMD/(μm) | 26.4 |

EXAMPLE 4

The following example demonstrates that microcapsules comprising a suspension of thiamethoxam particles can be spray dried to give a dry granular product. Microcapsules comprising a suspension of thiamethoxam particles were prepared according to the method described in Example 1, using water plus the ingredients given in the recipe of Table 4 below [later the water was removed to give a formulation having the recipe of Table 4]. Then this microcapsule suspension was mixed with an aqueous solution of polyacrylic acid (MW 2000), dextrin and Polyfon™ T (sodium lignosulfonate supplied by MeadWestvaco) to give a spray slurry. The slurry was spray dried in a Pepit™ WG4 spray drier to give a dry granular product with the following composition:

TABLE 4

| Component (% w/w) | |
|---|---|
| Components present in CS formulation | |
| Thiamethoxam | 30 |
| Solsperse 17000 | 1.98 |
| Rapeseed oil | 20.55 |
| Desmodur Z4470 SN | 16.94 |
| Gohsenol GL05 | 8.91 |
| Diethylenetriamine | 1.69 |
| Avicel CL611 | 2.63 |
| Components added in spray slurry | |
| Polyacrylic acid (MW2000) | 7.72 |
| Polyfon T | 6.67 |
| Dextrin | 13.13 |

EXAMPLE 5

The following example [using the products from Examples 1a to 1f] demonstrates that encapsulation of a suspension of thiamethoxam particles allows control over the release rate of the pesticide into water, with T50 values across the range from a few hours to several years.

Release rate measurements into water were carried out according to the following methodology. A capsule suspension was diluted into deionised water to give a concentration of typically 0.01% w/w thiamethoxam (i.e. well below its solubility limit).

This dispersion was rolled continuously for up to 4 weeks at 20° C. Aliquots were taken at various time-points, filtered through a 0.45 µm filter to remove the intact capsules, and then analysed for thiamethoxam. The results obtained are shown in FIG. 1.

EXAMPLE 6

Figure 2:
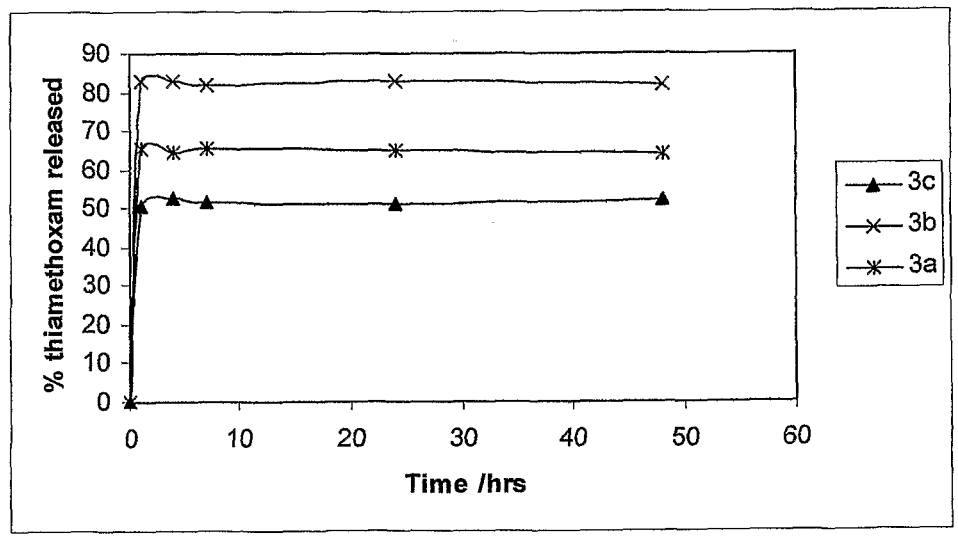

The following example [using the products from Examples 3a to 3c] illustrates that varying the ratio of encapsulated to unencapsulated thiamethoxam allows the release rate profile to be fine tuned to give a desired amount of freely available thiamethoxam followed by a slower release of the remaining active compound. The release rate methodology is as described in Example 5; the results are given in FIG. 2.

EXAMPLE 7

Figure 3:
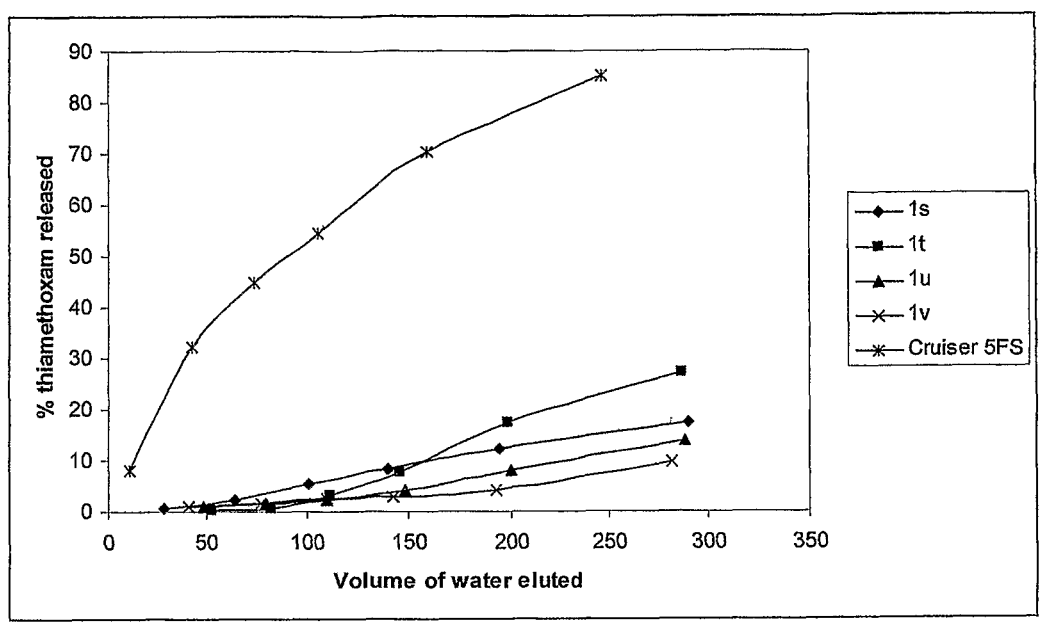

The following example [using the products from Examples 1s-1v] demonstrates that encapsulation of a suspension of thiamethoxam particles allows extended control over the release rate of the pesticide into soil when applied as a seed treatment (compared to non-encapsulated thiamethoxam as Cruiser™ 5FS (a suspension concentrate containing 500 g/l thiamethoxam). The microcapsule suspensions were mixed with a coating polymer Spectrum™ 300C and applied to maize seeds in a seed treater so as to give a loading of 1.25 mg thiamethoxam and 0.625 mg Spectrum 300C per seed. Ten treated seeds were placed on approximately 80 g soil in a Buchner funnel (pore size 2, 11 cm diameter) and covered with an additional 35 g soil and a filter paper. Fixed amounts of water (70 ml, 40 ml, 40 ml, 40 ml, 60 ml, 100 ml) were sprayed onto the filter paper, and the eluent was collected, weighed and analysed for thiamethoxam content; results are given in FIG. 3.

EXAMPLE 8

The following example demonstrates that encapsulation of thiamethoxam can result in extended systemic biological control when applied as a soil insecticide (compared to non-encapsulated thiamethoxam). Microcapsule suspension [from Example 1a] and Actara® WG [25% non-encapsulated thiamethoxam, by weight] were each individually applied to cucumber plants (variety Sakarta) at a rate of 5 mg thiamethoxam per plant. The application was carried out directly in the planting hole immediately before planting a seedling (the microcapsules were diluted in 3 ml water and Actara® WG was applied dry). The plot was irrigated before application and transplantation to reach field capacity, then irrigated with water [6 mm/m$^2$] every second day following transplantation. Every 2-3 days, the two youngest fully grown leaves were picked, and one leaf disc was punched out from each leaf (talking 4 plants per sampling time, using different plants for each sampling).

The leaf discs were exposed to approximately 25 adult whitefly (*Beinisia tabaci*) and cultivated in a Petri dish of 2% Agar gel. Mortality was assessed after 72 hours. Fully grown leaves continued to be picked until a day was reached when the measured mortality fell below 60%. As the table below shows, it was found that a 35% increase in persistence of bioefficacy of thiamethoxam was observed in the microcapsule suspension 1a compared to the non-encapsulated standard.

| Persistence of bioefficacy vs. *Bemisia tabaci* | |
|---|---|
| Formulation | Persistence of bioefficacy ≥ 60% |
| Actara ™ WG | 17 days |
| Example 1a | 23 days |

EXAMPLE 9

The following example demonstrates that encapsulation of thiamethoxam can result in reduced leaching when applied as a soil insecticide (compared to non-encapsulated thiamethoxam). Microcapsule suspensions [products from Examples 1d, 1k and 1l ] and Actara® WG [25% non-encapsulated thiamethoxam, by weight] were each individually applied to cucumber plants (variety Sakarta) at a rate of 5 mg thiamethoxam per plant. The application was carried out directly in the planting hole immediately before planting the seedling (the microcapsules were diluted in 3 ml water and Actara® WG was applied dry). The plot was irrigated before application and transplantation to reach field capacity, then irrigated with water [6 mm/m$^2$] every second day following transplantation. After various time intervals, soil cores were taken to depths of 0-18 cm and 18-36 cm directly below the plants (four cores per sampling time). 100 g of the soil was placed in a beaker (2 replicates) and made up to an overall volume of 140 ml with water. The slurries were stirred, then left for 30 minutes to allow the soil to sediment. Then 2.5 ml of the supernatant was taken from each subsample and recombined (4 replicates); broad bean seedlings infested with *Aphis craccivora* were cultivated in the supernatant and mortality was assessed after 72 hours. Up to a 3-fold reduction in leaching was observed for encapsulated formulations of thiamethoxam (compared to the non-encapsulated standard; see data below, where DAA=days after application).

| % mortality of *Aphis craccivora* (soil water from 18-36 cm depth) | |
|---|---|
| Trial B2 | % mortality (16DAA) |
| Actara™ WG | 45 |
| Example 1d | 21 |
| Trial D2 | % mortality (17DAA) |
| Actara® WG | 59 |
| Example 1k | 19 |
| Example 1l | 21 |

EXAMPLE 10

This example demonstrates that encapsulation of thiamethoxam [using products from Examples 1c and 1d] can result in extended biological control when used as a termiticide (compared to non-encapsulated thiamethoxam; Actara®WG [25% non-encapsulated thiamethoxam, by weight]). A traditional concrete slab study was carried out according to the following methodology at a trial site with a heavy infestation of *Coptotermes curvignathus*. The ground was cleared and wooden frames were installed around the individual areas to be treated (5 replicates per treatment). The ground was drenched with the termiticide treatments (thiamethoxam at either 0.1% or 0.2%) at an application volume of 4.5 liters/m² and the treated soil was covered with a vapour barrier (with a pipe cut into the barrier to expose a portion of the treated soil). Then concrete was applied on top of the vapour barrier. A wooden block was inserted into the pipe, and the pipe was sealed with a cap. Assessments of termite damage to the wooden block were made at monthly intervals, replacing the damaged blocks with new blocks at each assessment point.

In this trial (where any Wood Damage Index [WDI] value above 1 represents a failure of the treatment), it was found that the non-encapsulated standard of thiamethoxam failed at both 0.1 and 0.2% treatment rates of thiamethoxam after 10 months. However, encapsulated formulations showed no failures at either thiamethoxam rate after 12 months.

| Termite damage as assessed by WDI (scores over 5 replicates) | | | | |
|---|---|---|---|---|
| | WDI (10 months, 0.2% AI) | WDI (10 months, 0.1% AI) | WDI (12 months, 0.2% AI) | WDI (12 months, 0.1% AI) |
| Actara® WG | 1, 2, 1, 1, 1 | 1, 3, 1, 2, 1 | 1, 3, 1, 1, 1 | 1, 3, 1, 5, 1 |
| Example 1c | 1, 1, 1, 1, 1 | 1, 1, 1, 1, 1 | 1, 1, 1, 1, 1 | 1, 1, 1, 1, 1 |
| Example 1d | 1, 1, 1, 1, 1 | 1, 1, 1, 1, 1 | 1, 1, 1, 1, 1 | 1, 1, 1, 1, 1 |

EXAMPLE 11

This example illustrates that encapsulation of thiamethoxam [product of Example 1i] can result in greater biological efficacy when used as a seed treatment, particularly under conditions of high pest pressure (compared to non-encapsulated thiamethoxam; Cruiser® FS). Thiamethoxam formulations were individually applied to maize seeds at a rate of 1.25 mg thiamethoxam per seed & tested for efficacy against corn rootworm (*Diabrotica* spp.) at several field locations. The experimental design was a randomized complete block with 4 replications. Each plot consisted of four 35-seed rows, 5.3 m in length, planted using a 4-row cone planter. Planting, cultivation, fertility management, irrigation and harvesting varied among locations based on local corn management practices. Seedling emergence was evaluated by counting emerged plants in the centre two rows at 14, 21 and 28 days after planting.

Evaluation of corn rootworm damage was made when it was estimated that rootworm feeding was finished, when most of the observed larvae in soil samples from the root zone were third instar larvae [i.e. nearing maturation and no longer feeding on roots]. Five plants from each of the outer two rows of each plot (total of 10 plants/plot) were dug up and washed to remove attached soil.

Root damage ratings for all locations were performed according to the Node-Injury Scale (Oleson, J. D. et al. 2005, J Econ Entomol 98(1): 1-8): 0=no feeding damage, 1=one node or the equivalent of an entire node eaten back to within approximately 2 inches (5 cm) of the stalk, 2=two complete nodes (or equivalent) eaten, 3=three or more nodes (or equivalent) eaten. Damage in between complete nodes was noted as the percentage of the node eaten. The rating for each plot/rep is the mean of the 10 harvested plants.

| Efficacy against corn rootworm as assessed using the linear root rating scale (a lower number equates to less root damage) | | |
|---|---|---|
| | Root rating (normal pest pressure) | Root rating (high pest pressure) |
| Cruiser® FS | 0.9 | 1.6 |
| Example 1i | 0.7 | 1.0 |

The invention claimed is:

1. A product comprising microcapsules, said microcapsules comprising:
    (a) a polymeric shell; and
    (b) a core encapsulated by said polymeric shell, said core comprising (i) a solid agrochemical dispersed in a (ii) matrix material, said solid agrochemical having a water-solubility in the range of 0.1 to 100 g/l at 20° C., and (iii) a water-immiscible liquid, the matrix being distributed non-continuously throughout the water-immiscible liquid.

2. A product as claimed in claim 1 where the agrochemical is a neonictinoid insecticide.

3. A product as claimed in claim 2 where the agrochemical is acetamiprid, clothianidin, imidacloprid, thiacloprid or thiamethoxam.

4. A product as claimed in claim 3 where the agrochemical is thiamethoxam.

5. A product as claimed in claim 1 where the microcapsules are dispersed in an aqueous phase.

6. A product as claimed in claim 1 where the product is a dry product.

7. A product as claimed in claim 6 where the dry product is granular.

8. A product as claimed in claim 6 where the dry product is water-dispersible.

9. A product as claimed in claim 5 where the aqueous phase comprises an agrochemical.

10. A product as claimed in claim 9 where the agrochemical in the aqueous phase has a water-solubility in the range of 0.1 to 100 g/l at 20° C.

11. A product as claimed in claim 10 where the agrochemical in the aqueous phase is a neonictinoid insecticide.

12. A product as claimed in claim 11 where the agrochemical in the aqueous phase is acetamiprid, clothianidin, imidacloprid, thiacloprid or thiamethoxam.

13. A product as claimed in claim 12 where the agrochemical in the aqueous phase is thiamethoxam.

14. A product as claimed in claim 1 where the matrix material is a polymer comprising a polyurea, a polyamide, a polyurethane, or a mixture thereof.

15. A product as claimed in claim 14 where the matrix material is a polyurea.

16. A product as claimed in claim 1 where the polymeric shell is a polymer comprising a polyurea, a polyamide, a polyurethane, or a mixture thereof.

17. A product as claimed in claim 16 where the polymeric shell is a polyurea.

18. A product as claimed in claim 1 where the water-immiscible liquid has a water solubility of less than or equal to 5000 ppm by weight at 20° C.

19. A product as claimed in claim 1 where the water-immiscible liquid comprises an agrochemical.

20. A process for preparing a product as claimed in claim 1 comprising the step of interfacial polymerisation of an oil-in-water emulsion in which a solid agrochemical is dispersed within an oil.

21. A product as claimed in claim 1 where the matrix material comprises a polymeric material.

22. A product as claimed in claim 14 where the polymeric shell comprises a polymer comprising a polyurea, a polyamide, a polyurethane, or a mixture thereof.

23. A product as claimed in claim 22 where the polymeric shell comprises a polyurea.

24. A product comprising microcapsules, said microcapsules comprising:
   (a) a polymeric shell comprising a polyurea, a polyamide, a polyurethane, or a mixture thereof; and
   (b) a core encapsulated by said polymeric shell, said core comprising:
      (i) a water-immiscible liquid,
      (ii) a matrix material distributed non-continuously throughout the water-immiscible liquid, and
      (iii) a solid agrochemical having a water-solubility in the range of 0.1 to 100 g/l at 20° C., said solid agrochemical being within said matrix material.

* * * * *